United States Patent [19]
Monkhouse

[11] 3,952,004
[45] Apr. 20, 1976

[54] STABILIZED E-SERIES PROSTAGLANDINS
[75] Inventor: Donald C. Monkhouse, Waterford, Conn.
[73] Assignee: Pfizer Inc., New York, N.Y.
[22] Filed: Aug. 1, 1975
[21] Appl. No.: 601,037

Related U.S. Application Data
[62] Division of Ser. No. 480,354, June 18, 1974, abandoned.

[52] U.S. Cl. .................. 260/308 D; 260/468 D; 260/514 D; 260/559 R; 424/269; 424/305; 424/317; 424/318; 424/320
[51] Int. Cl.$^2$ ............ A61K 31/16; A61K 31/19; C07C 61/38; C07D 257/06
[58] Field of Search .......... 424/305, 317, 318, 320, 424/269; 260/308 D, 468 D, 559 R, 514 D

[56] References Cited
UNITED STATES PATENTS
3,755,599  8/1973  Rosenthale et al. ............. 424/318
3,826,823  7/1974  O'Rourke et al. ............... 424/318
3,851,052  11/1974  Monkhouse ..................... 424/318

Primary Examiner—Sam Rosen
Attorney, Agent, or Firm—Connolly and Hutz

[57] ABSTRACT

A lyophilized pharmaceutical composition comprising a prostaglandin of the E-series and an excipient selected from the group consisting of sodium chloride, cyclodextrin, succinic acid and polyvinylpyrrolidone.

11 Claims, No Drawings

STABILIZED E-SERIES PROSTAGLANDINS

CROSS-REFERENCE TO RELATED APPLICATION

This application is a division of application Ser. No. 480,354 filed June 18, 1974 and now abandoned.

BACKGROUND OF THE INVENTION

The prostaglandins are C-20 unsaturated fatty acids which exhibit diverse physiological effects. The prostaglandins of the E-series are those which have at the nine position a carbonyl group and a hydroxy function at the eleven position.

The prostaglandins of the E-series are potent vasodilators (Bergstrom et al., Acta Physiol. Scand. 64:332-33, 1965 and Life Sci. 6:449-455, 1967) and lower systemic arterial blood pressure on intravenous administration (Weeks and King, Federation Proc. 23:327, 1964; Carlston et al., Acta Physiol. Scand. 75:161-169, 1969). Another well known physiological action for $PGE_1$ and $PGE_2$ is as a bronchodilator (Cuthbert, Brit. Med. J. 4:723-726, 1969). Still another important physiological role for the natural prostaglandins is in connection with the reproductive cycle. $PGE_2$ is known to possess the ability to induce labor (Karim et al., J. Obstet. Gynaec. Brit. Cwlth. 77:200-210, 1970), to induce therapeutic abortion (Bygdeman et al., Contraception, 4:293, 1971) and to be useful for control of fertility (Karim, Contraception 3:173, 1971). Patents have been obtained for several prostaglandins of the E-series as inducers of labor in mammals (Belgian Patent No. 754,158 and West German Patent No. 2,034,641).

Still other known physiological activities for $PGE_1$ are in the inhibition of gastric acid secretion (Shaw and Ranwell, Worcester Symposium on Prostaglandins, New York, Wiley, 1968, p. 55–64) and also of platelet aggregation (Emmons et al., Brit. Med. J. 2:468–472, 1967).

SUMMARY OF THE INVENTION

The present invention comprises a lyophilized pharmaceutical composition containing a biologically active E-series prostaglandin together with a storage stabilizing amount of solid diluent in a weight/weight ratio of 1:1 to 1:200 selected from the group consisting of sodium chloride, cyclodextrin, polyvinylpyrrolidone and succinic acid.

DETAILED DESCRIPTION OF THE INVENTION

The synthesis of the natural prostaglandins of the E-series is described by Corey et al., J. Amer. Chem. Soc., 92:2586, 1970, and references cited therein. E-series prostaglandins made by the reported reaction sequences as well as those made by other schemes or isolated from natural materials are suitable for use in the compositions of this invention. Also suitable in the processes of this invention are 15-lower alkyl derivatives of the natural prostaglandins such as those described by Bundy et al., Anal. N.Y. Acad. Sci., 180, p. 76, 1971.

The N-substituted prostaglandin carboxamides such as N-acetyl and N-benzoyl-$PGE_2$ carboxamides described in U.S. Ser. No. 260,518 filed June 7, 1972; the tetrazoyl derivatives of prostaglandins disclosed in U.S. Ser. No. 177,102 filed Sept. 1, 1971; the oxaprostaglandins disclosed in U.S. Ser. No. 259,215 filed June 2, 1972; the p-biphenyl esters of w-nor substituted prostaglandins such as 16-phenyl-13,14-dihydro-w-tetranor $PGE_2$ p-biphenyl ester described in U.S. Ser. No. 304,815 filed Nov. 8, 1972, the substituted pentanorprostaglandins such as 16-p-biphenyl-w-tetranor $PGE_2$ and 16-($\alpha$-thienyl)-w-tetranor $PGE_1$ disclosed in U.S. Ser. No. 271,220 filed July 13, 1972; and compounds such a N-methanesulfonyl-16-phenoxy-w-tetranor-$PGE_2$ carboxamide covered in U.S. Ser. No. 304,813 filed Nov. 8, 1972 are especially important examples of biologically active prostaglandins of the E-series useful in the compositions of the present invention. The disclosures of the above named U.S. patent applications are incorporated herein by reference.

For the first step in the preparation of the N-substituted prostaglandin carboxamides, the appropriate hemiacetal precursor is caused to react with the disodium salt of a novel N-substituted carboxamide butyltriphenylphosphonium bromide, in a molar ratio of from about 1:2 to 1:5. Such precursors are as follows:

2-[5$\alpha$-hydroxy-3$\alpha$-(tetrahydropyran-2-yloxy)-2$\beta$-(3$\alpha$-(tetrahydropyran-2-yloxy)-trans-1-octen-1-yl)cyclopent-1$\alpha$-yl]acetaldehyde, $\gamma$-hemiacetal for $PGE_1$, $PGE_2$, and 13,14-dihydro-$PGE_1$;

2-[5$\alpha$-hydroxy-3$\alpha$-(tetrahydropyran-2-yloxy)-2$\beta$-(3$\beta$-lower alkyl-3$\alpha$-(tetrahydropyran-2-yloxy)-trans-1-octen-1-yl)cyclopent-1$\alpha$-yl]acetaldehyde, $\gamma$-hemiacetal for the 15-lower alkyl derivatives of these same prostaglandins;

2-[5$\alpha$-hydroxy-3$\alpha$-(tetrahydropyran-2-yloxy)-2$\beta$-(3$\alpha$-(tetrahydropyran-2-yloxy)oct-1-yl]cyclopent-1$\alpha$-yl]acetaldehyde, $\gamma$-hemiacetal for 13,14-dihydro-$PGE_2$;

2-[5$\alpha$-hydroxy-3$\alpha$-(tetrahydropyran-2-yloxy)-2$\beta$-(3$\beta$-lower alkyl-3$\alpha$-(tetrahydropyran-2-yloxy)-oct-1-yl]cyclopent-1$\alpha$-yl]acetaldehyde, $\gamma$-hemiacetal for the 15-lower alkyl derivatives of 13,14-dihydro-$PGE_2$;

and 2-[5$\alpha$-hydroxy-3$\alpha$-(tetrahydropyran-2-yloxy)-2$\beta$-(3$\alpha$-(tetrahydropyran-2-yloxy)-cis-5-trans-1-octadien-1-yl)cyclopent-1$\alpha$-yl]acetaldehyde, $\gamma$-hemiacetal for $PGE_3$.

These hemiacetal precursors are prepared by the following reaction sequences wherein PBP is p-biphenyl, THP is 2-tetrahydropyranyl, and R is lower alkyl.

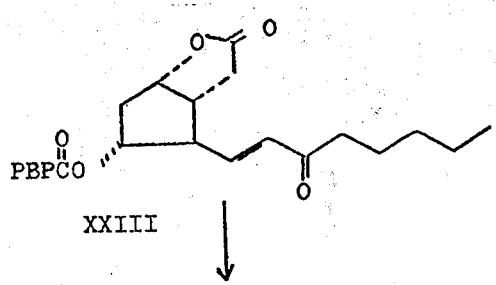

XXIII

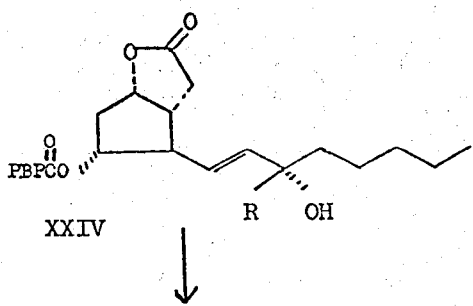
XXIV
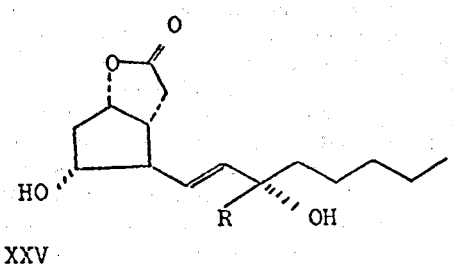
XXV
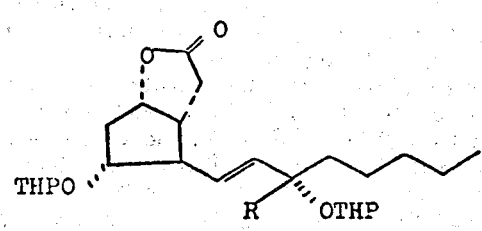
XXVI
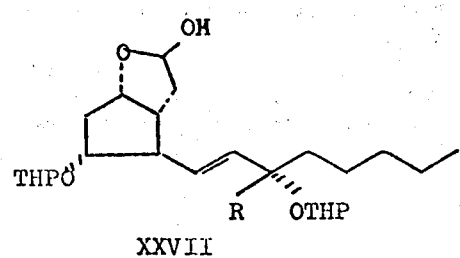
XXVII
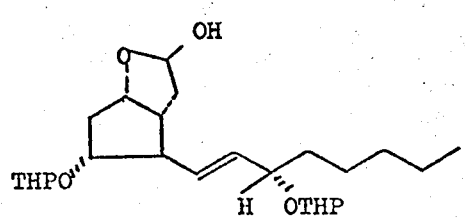
I

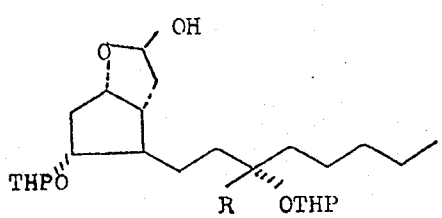

XXVIII

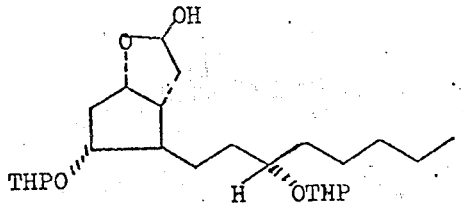

VI

Compound XXIII is a known compound and is prepared by the method of Corey et al., J.A.C.S., 93:1491, 1971. It is treated with alkyl lithium to produce Compound XXIV.

Compound XXIV → Compound XXV is a transesterification reaction brought about by treatment with $K_2CO_3$/methanol.

Compound XXV is treated with dihydropropan in the presence of an acid catalyst to produce Compound XXVI.

Compound XXVI is reduced with di-isobutyl aluminum hydride to produce the unsaturated hemiacetal Compound XXVII.

Compound XXVII is reduced with $H_2$/Pd to give the saturated hemiacetal XXVIII.

Alternatively, Compound XXIII can be reduced with zinc borohydride to produce Compound XXIV wherein R is hydrogen. This latter compound may be carried through an analogous series of steps to produce hemiacetals I and VI.

The substituted carboxamide-containing intermediates may be converted by published procedures (Corey et al., J. Am. Chem. Soc., 93:1490, 1971) to the N-substituted carboxamide analogs of the prostaglandins listed herein. The steps entailed are summarized in the reaction schems A and B below, wherein R is alkanoyl, cycloalkanoyl or alkenoyl of from 2 to 10 carbon atoms; aryoyl or substituted aryoyl from 7 to 11 carbon atoms wherein said substituents may be methyl, halogen or methoxy; alkylsulfonyl from 1 to 7 carbon atoms; phenylsulfonyl or mono-substituted phenylsulfonyl wherein said substituent may be methyl, halogen or methoxy; styrylsulfonyl; or 2-thiophenesulfonyl; and THP is tetrahydropyranyl.

The utility of these prostaglandins is the same as for the naturally occurring E-series prostaglandins. For example, a reconstituted lyophilized solution of N-methanesulfonyl-$PGE_2$ is employed to induce midtrimester abortion using an extra-amniotic injection of from 0.1 to 10 mg per dose. For initiation of menses in very early pregnancy, a reconstituted lyophilized solution of N-N-methanesulfonyl-$PGE_2$ carboxamide is given by intrauterine administration using a dose from 0.05 to 5 mg.

REACTION SCHEME A.

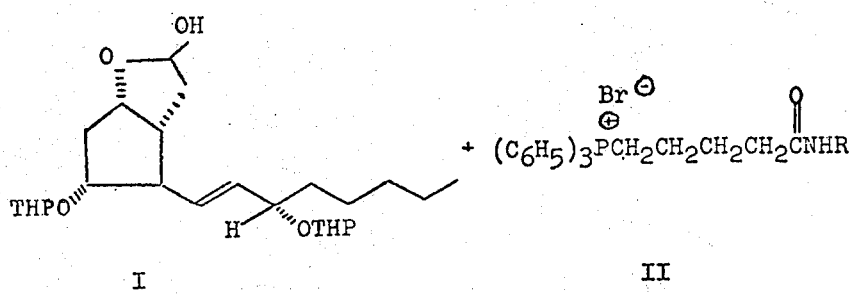

I            II

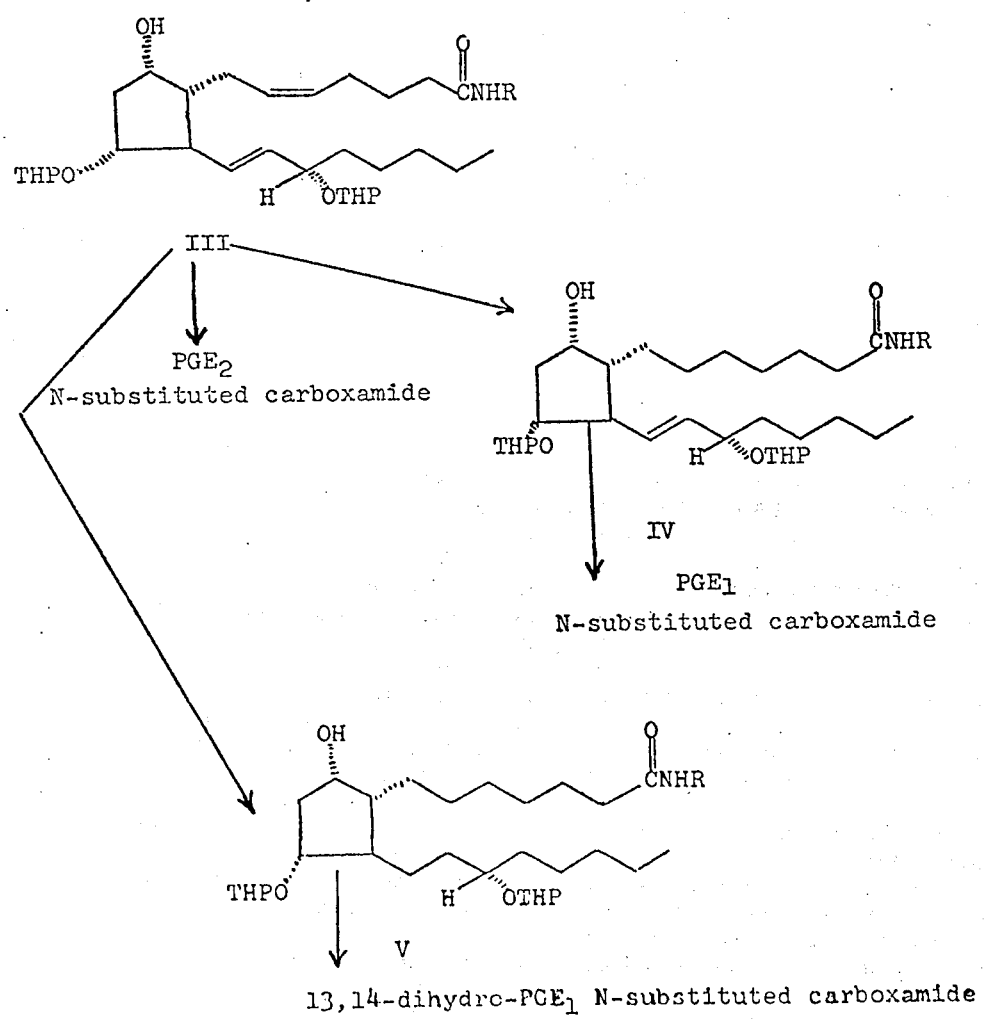
REACTION SCHEME B
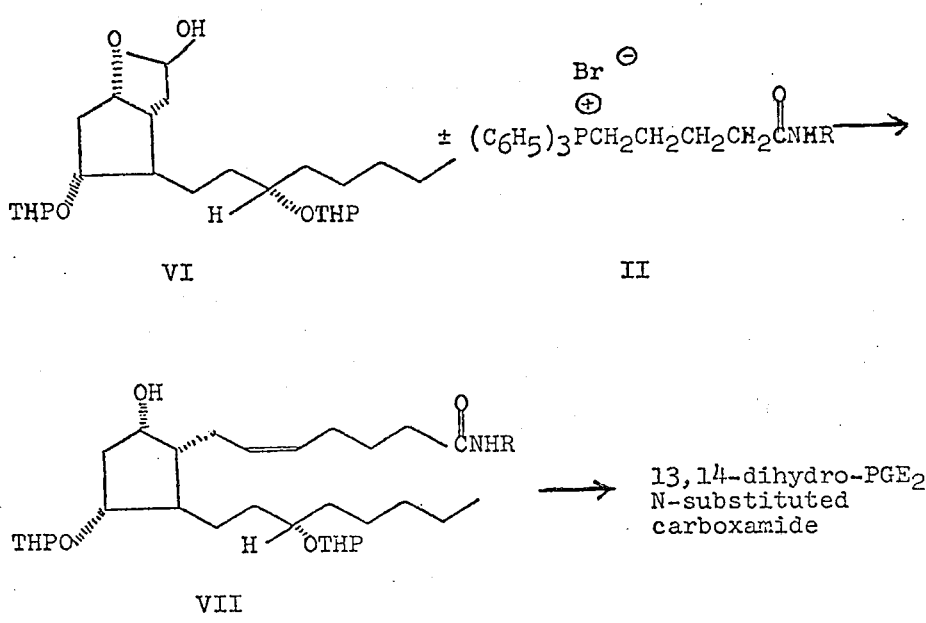

As shown in Reaction Scheme A, Hemiacetal I is caused to react with the novel reagent II to produce III, the N-substituted carboxamide analog of the bis-THP ether of PGF$_2\alpha$.

III → PGE$_2$-N-substituted carboxamide requires treatment with Jones reagent to form a second intermediate before the acid treatment and purification as above.

III → PGE$_1$-N-substituted carboxamide requires selective reduction with palladium on carbon methanol to produce IV which then follows exactly the same method as outlined for PGE$_2$ above.

III → 13,14-dihydro-PGE$_1$ N-substituted carboxamide requires a reduction with palladium on carbon in methanol to produce V which is then treated as for E$_2$ in exactly the same method as outlined above.

To produce the other 13,14-dihydro derivatives one follows the procedures outlined above. Alternatively the PGE$_2$-N-substituted carboxamides may be reduced with palladium on carbon in methanol to produce the 13,14-dihydro-PGE$_1$-N-substituted carboxamide.

Referring now to Reaction Scheme B, Hemiacetal VI is caused to react with the novel reagent II to produce VII, the N-substituted carboxamide analog of the bis-THP ether of 13,14-dihydro PGF$_2$.

VII → 13,14-dihydro PGE$_2$-N-substituted carboxamide requires treatment with Jones reagent to form a second intermediate before acid treatment and purification as above.

To produce the 15-lower alkyl derivatives of all of the above mentioned prostaglandin N-substituted carboxamides, one merely employs a hemiacetal I or hemiacetal VI with a lower alkyl moiety in the 15 position and proceeds as above to produce the desired compound.

To produce PGE$_3$ N-substituted carboxamide, hemiacetal VIII is employed as the starting material and all of the other reaction steps are identical to those given above.

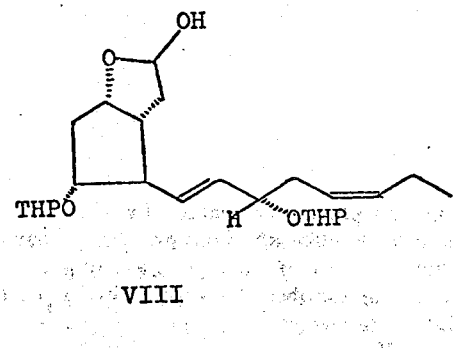

VIII

REACTION SCHEME C

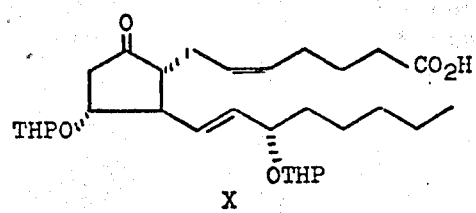 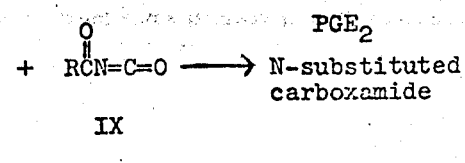

X

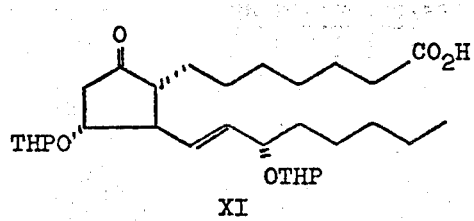 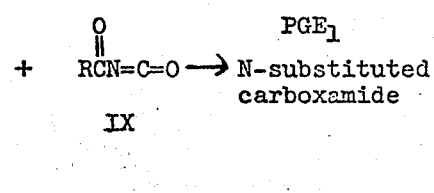

XI

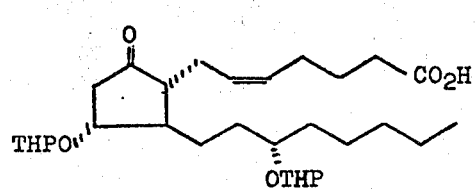 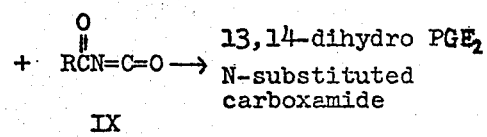

XII

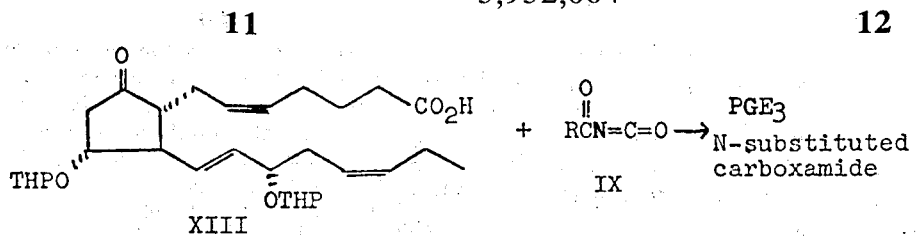

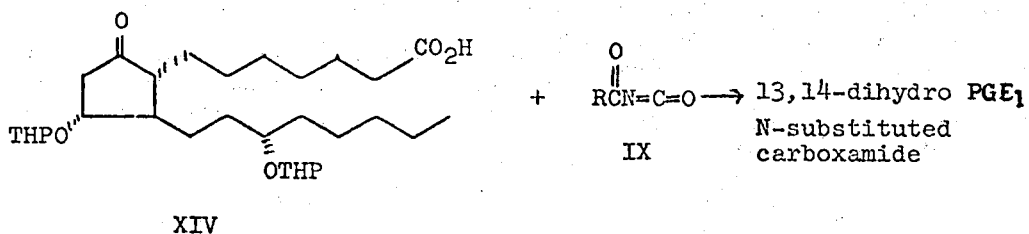

Alternatively, the N-substituted prostaglandin carboxamides may be prepared by treating the appropriate prostaglandin acid precursors with an acyl isocyanate followed by hydrolysis of the tetrahydropyranyl groups as outlined in Reaction Scheme C. The appropriate precursors X-XIV are known compounds (Corey, et al., J. Am. Chem. Soc., 92, 397 (1970); ibid., 92, 2586 (1970); ibid., 93, 1490 (1971)).

For the first step in the preparation of the tetrazoyl derivatives of prostaglandins, the appropriate hemiacetal precursor (I, VI, VIII) is caused to react with the disodium salt of a novel tetrazoylbutyltriphenylphosphonium bromide (XV), in a molar ratio of from about 1:2 to 1:5. Such precursors may be converted to the tetrazoyl analogs of any of the prostaglandins listed as described above for the N-substituted carboxamide analogs.

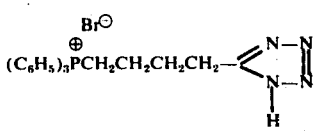

REACTION SCHEME D

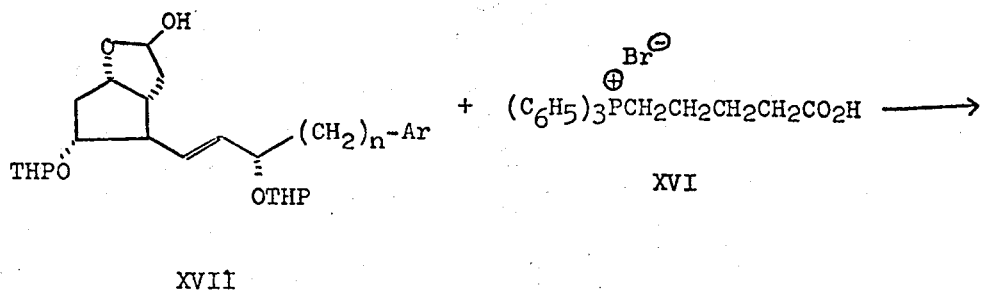

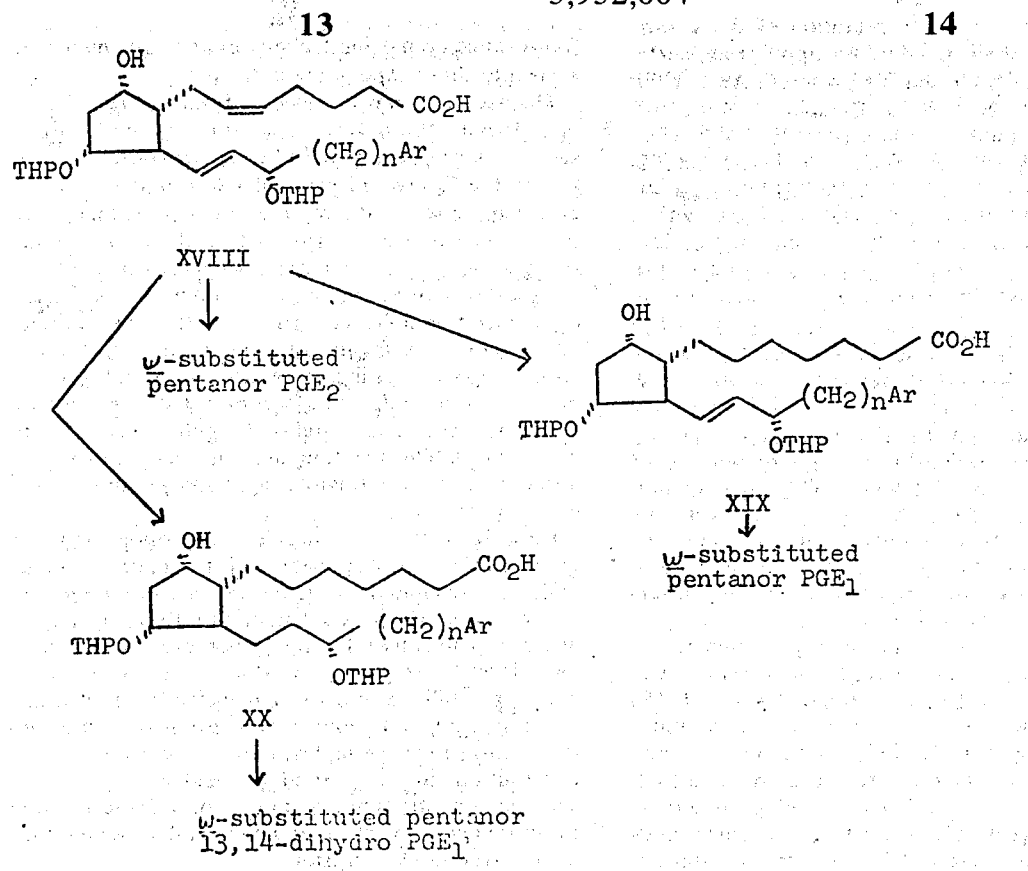
REACTION SCHEME E
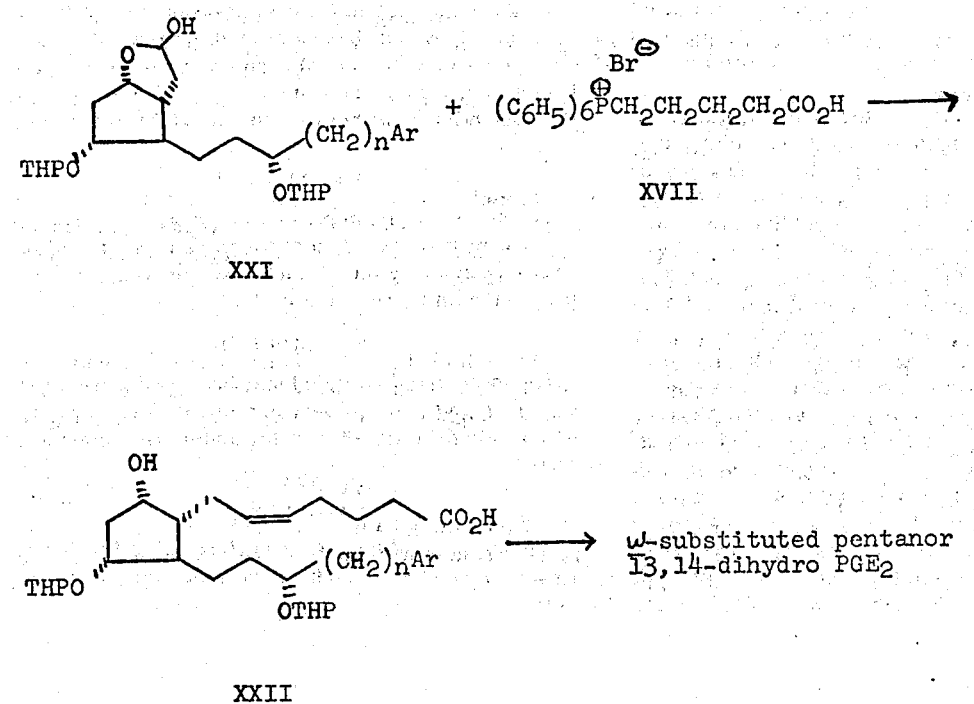

For the first step in the preparation of the w-substituted pentanor prostaglandins, the appropriate hemiacetal precursors (XVII and XXI wherein Ar is $\alpha$- or $\beta$-furyl, $\alpha$- or $\beta$-thienyl, $\alpha$- or $\beta$-naphthyl, 3,4-dimethoxyphenyl, 3,4-methylenedioxyphenyl, 3,4,5-trimethoxyphenyl, phenyl, or mono-substituted phenyl wherein said substituent is halo, trifluoromethyl, phenyl, lower alkyl, or lower alkoxy, and n is 1 or 2) is caused to react with the disodium salt of the known carboxybutyltriphenylphosphonium bromide (XVI), in a molar ratio of from 1:2 to 1:5. The products of this reaction (XVIII and XXII) may be converted to the w-substituted pentanor prostaglandins as outlined in Reaction Schemes D and E and described above for the N-substituted carboxamide analogs.

Treatment of the appropriate w-substituted pentanor PGE analog with a substituted carbodiimide, for example dicyclohexylcarbodiimide, and p-phenylphenol in a molar ratio of 1:1:10 in a solvent such as methylene chloride or chloroform provides after column chromatographic purification the desired p-biphenyl esters of w-substituted pentanor PGE analogs.

The application of prostaglandins in a number of areas has been severely hampered by their instability in solution. Karim et al., (Eur. J. Pharmacol. 4:416, 1968) measured the biological activity of saline solutions containing 100 ng/ml $PGE_1$, $PGE_2$ and $PGF_{2\alpha}$ stored at various pH values at room temperature. The PGE compounds showed 25–40% loss of biological activity after 60 days at pH 5–7, while the PGF compounds were still fully active after 182 days. Other prostaglandin stability studies have been carried out by Andersen (J. Lipid Res., 10:320, 1969), Brummer (J. Pharm. Pharmacol., 23:804, 1971) and others and show similar results.

Lyophilization (freeze-drying) has been an accepted procedure for storing biologically active substances that are unstable in solution since the early penicillin days. Lyophilization is the term given to the process whereby ice is sublimed from frozen solutions leaving a dry porous mass of approximately the same size and shape as the original frozen mass. In this manner a compound that is heat-sensitive and undergoes rapid decomposition in aqueous solution can be formulated into a stable form which is readily reconstituted for parenteral injection.

Most prostaglandins can be satisfactorily freeze-dried to give chemically and physically stable solid plugs. However, there are a number of prostaglandins such as Prostaglandin $E_2$ which may freeze dry to an unsatisfactory oily mass. This necessitates the addition of a solid diluent in the freeze drying process to provide a suitable matrix for the biologically active compound. This technique allows the storage of the drug in a solid state over an extended period of time. Depending on the solubility characteristics of the prostaglandin, reconstitution may be made with physiological saline or dextrose solution, propylene glycol or aqueous ethanol.

The prostaglandin is added to a small amount of water containing sufficient co-solvent such as ethanol, dimethylacetamide and tertiary butanol to bring the compound into solution. An excipient is added at a weight/weight ratio of prostaglandin to excipient of about 1:1 to 1:200, preferably 1:20. The solution is sterilized by filtration through a bacterial filter and freeze-dried employing techniques and equipment well known to those experience in the art.

The excipient may be selected from a range of compounds with the notable exception of simple sugars such as lactose and mannitol which promote dehydration in the E-series of prostaglandins. Suitable excipients may be selected from the group consisting of sodium chloride, cyclodextrin, polyvinylpyrrolidone and succinic acid. These materials when lyophilized with the prostaglandin yield plugs of good bulk. The degree of stabilization afforded varies with the prostaglandin and selected excipient. In general, polyvinylpyrrolidone provides a superior matrix for stabilizing the prostaglandin molecule. Reconstituted samples are tested for chemical stability (directly correlated to biological stability) by thin layer chromatography visualized by 254 nm ultraviolet light and phosphomolybdic acid spray.

Regardless of the nature of the prostaglandin, its lyophilization and dispersion with the matrices of the selected excipient is a stable and preferred form in which to store the prostaglandin prior to reconstitution and use by injection. Lyophilization provides a convenient form for shipment and storage, and obviates the need for stability protection at deep freeze or refrigerator temperatures. Lyophilization also provides flexibility of dosage for the highly active prostaglandins. Reconstitution may be varied to yield a concentrated solution for intramuscular injection, a dilute solution for intravenous injection or a highly dilute solution for administration by perfusion.

EXAMPLE I

To aliquots of a solution of Prostaglandin $E_2$ (10 mg) in 20 ml of water and 0.2 ml of ethanol are added each of the following excipients at a weight/weight of prostaglandin to excipient of 1:20: cyclodextrin, sodium chloride, succinic acid and polyvinylpyrrolidone. The individual solutions are sterilized by passage through bacterial filters, transferred to sterile vials and then freeze-dried.

There is no significant change in chemical stability after storage for about 6 weeks at room temperature as determined by thin layer chromatography, ultraviolet light spectrometry and phosphomolybdic acid spray. Under the same conditions, freeze-dried samples of Prostaglandin $E_2$ without excipient exhibit severe degradation.

EXAMPLE II

The method of Example I may be repeated with comparable results with dimethylacetamide as the co-solvent in place of ethanol, and a weight/weight ratio of prostaglandin to excipient of 1:1.

EXAMPLE III

The method of Example I may be repeated with comparable results with tertiary-butanol in place of ethanol and a weight/ratio of prostaglandin to excipient of 1:200.

EXAMPLE IV

The method of Example I may be repeated with comparable results with each of the following prostaglandins:

N-methanesulfonyl-16-phenoxy-w-tetranor-PGE$_2$ carboxamide
2-descarboxy-2-(tetrazol-5-yl)-PGE$_2$
16-phenyl-13,14-dihydro-w-tetranor-PGE$_2$,p-biphenyl ester
16-phenoxy-w-tetranor-PGE$_2$,p-biphenyl ester
N-acetyl-PGE$_2$ carboxamide
N-benzoyl-PGE$_2$ carboxamide
N-methanesulfonyl-PGE$_2$ carboxamide
19-oxa-PGE$_2$
15-methyl-PGE$_2$

What is claimed is:

1. A lyophilized pharmaceutical composition comprising a biologically active prostaglandin of the E-series together with a storage stabilizing amount of sodium chloride in a weight/weight ratio of 1:1 to 1:200.

2. The composition of claim 1 wherein said prostaglandin is Prostaglandin E$_2$.

3. The composition of claim 1 wherein said prostaglandin is N-methanesulfonyl-16-phenoxy-w-tetranor-PGE$_2$ carboxamide.

4. The composition of claim 1 wherein said prostaglandin is 2-descarboxy-2-(tetrazol-5-yl)-PGE$_2$.

5. The composition of claim 1 wherein said prostaglandin is 16-phenyl-13,14-dihydro-w-tetranor-PGE$_2$, para-biphenyl ester.

6. The composition of claim 1 wherein said prostaglandin is 16-phenoxy-w-tetranor-PGE$_2$, para-biphenyl ester.

7. The composition of claim 1 wherein said prostaglandin is N-acetyl-PGE$_2$ carboxamide.

8. The composition of claim 1 wherein said prostaglandin is N-benzoyl-PGE$_2$ carboxamide.

9. The composition of claim 1 wherein said prostaglandin is N-methanesulfonyl-PGE$_2$ carboxamide.

10. The composition of claim 1 wherein said prostaglandin is 19-oxa-PGE$_2$.

11. The composition of claim 1 wherein said prostaglandin is 15-methyl-PGE$_2$.

* * * * *